United States Patent [19]

Parmer

[11] Patent Number: 5,264,832
[45] Date of Patent: Nov. 23, 1993

[54] PARALLEL CONDUCTOR CHIP DETECTOR

[75] Inventor: James D. Parmer, Phoenix, Ariz.

[73] Assignee: Allied-Signal Inc., Morris Township, Morris County, N.J.

[21] Appl. No.: 787,186

[22] Filed: Nov. 4, 1991

[51] Int. Cl.⁵ .............................................. G08B 17/10
[52] U.S. Cl. ..................................... 340/631; 73/61.42; 324/204
[58] Field of Search ..................... 340/631, 627, 607; 73/61.42, 61.71; 324/204, 693; 200/61.09

[56] References Cited

U.S. PATENT DOCUMENTS

| | | |
|---|---|---|
| 2,936,890 | 5/1960 | Botstiber . |
| 3,317,042 | 5/1967 | Botstiber . |
| 3,325,009 | 6/1967 | Botstiber et al. ............. 340/631 |
| 3,404,337 | 9/1968 | Pool et al. . |
| 3,553,672 | 1/1971 | Smith ............................ 340/631 |
| 4,008,464 | 2/1977 | Hobbie . |
| 4,100,491 | 7/1978 | Newman, Jr. et al. ......... 340/631 |
| 4,219,805 | 8/1980 | Magee et al. . |
| 4,298,478 | 11/1981 | Watson et al. . |
| 4,417,984 | 11/1983 | O'Meara, Jr. . |
| 4,519,919 | 5/1985 | Whyte et al. . |
| 4,564,448 | 1/1986 | O'Meara, Jr. . |
| 4,686,469 | 8/1987 | Lewis . |
| 4,734,202 | 3/1988 | Mach . |
| 5,179,346 | 1/1993 | McGee et al. ................. 340/631 |

Primary Examiner—Brent Swarthout
Attorney, Agent, or Firm—Jerry J. Holden; Robert A. Walsh

[57] ABSTRACT

A simpler, multiple element chip detector having two parallel, electrical conductors shrouding a plurality of discrete magnets which are aligned along the longitudinal axis of the chip detector is provided. The poles of each magnet abut opposite conductors defining a chip gap. A plurality of electrical isolators are mounted about the conductors and positioned between each of the magnets to define a chip element therebetween. The number of chip elements can be varied by adding or subtracting a magnet and isolator. The conductors are mounted in a housing to receive an electrical potential. Thus, regardless of the number of chip elements no additional circuitry is required. In an alternative embodiment the discrete magnets are replaced with a single magnet. In this embodiment the number of chip elements can be increased or decreased by only adding or removing an isolator.

18 Claims, 1 Drawing Sheet

PARALLEL CONDUCTOR CHIP DETECTOR

TECHNICAL FIELD

This invention relates to chip detectors for detecting the build up of ferromagnetic particles in a lubrication system, and in particular to a novel chip detector having two parallel conductors shrouding a permanent magnet which is disposed coincident with the longitudinal axis of the chip detector.

BACKGROUND OF THE INVENTION

The presence of ferromagnetic particles in the oil flow of a lubrication system such as the gearbox of a gas turbine engine is an indication of distress in the bearings and gears of the gearbox and engine which if not corrected could result in a catastrophic failure. A chip detector is an electrical device used to detect the buildup of such particles. Hobble, U.S. Pat. No. 4,008,464 discloses a typical chip detector comprised of two, spaced apart, annular magnets mounted on a common insulating member. Each magnet is discretely wired to an indicator circuit. As the oil flows over these magnets, ferromagnetic particles are captured by the flux lines between the magnets. When a sufficient number of particles have been captured, the gap between the two magnets is bridged to provide an electrical conducting path the resistance of which is low enough to permit electrical current to pass and actuate a warning light. The combination of magnets, and conductor to form a single chip gap is generally referred to as a chip element.

Some gearboxes have a plurality of adjacent oil flow paths each fluidly isolated from the other, and each requiring its own chip element. To meet this requirement, multiple element chip detectors have been built that have a plurality of chip elements radially stacked about the longitudinal axis of the detector so that the chip gaps are parallel with this axis. An insulating member is mounted between each of the chip elements to both electrically isolate each of the chip elements from ground and to prevent oil from leaking from one flow path to another.

A major disadvantage of these multiple element chip detectors is that they require a multiplicity of conductors, magnets and insulators as well as separate circuitry for each chip element.

Accordingly, there is a need for a simpler, multiple element chip detector that for a given number of flow paths has fewer parts and only a single electrical circuit.

SUMMARY OF THE INVENTION

An object of the present invention is to provide a simpler, multiple element chip detector that for a given number of flow paths has fewer parts and only a single electrical circuit.

Another object of the present invention is to provide a multiple element chip detector in which the number of chip elements is easily adjustable.

The present invention achieves the above-stated objects by providing a chip detector having two parallel, electrical conductors shrouding a plurality of discrete magnets which are aligned along the longitudinal axis of the chip detector. The north pole of each magnet is adjacent one of the conductors and the south poles are adjacent the other conductor. An electrical isolator is mounted about the conductors and positioned longitudinally between each of the magnets to define a chip element. The number of chip elements can be varied by adding or subtracting magnets and isolators. The conductors are mounted in a housing and receive an electrical potential. Thus, regardless of the number of chip elements, there is only one electrical circuit defined by the conductors. In yet a simpler embodiment, the discrete magnets are replaced with a single continuous magnet that spans the longitudinal length of the conductors. In this embodiment the number of chip elements can be increased or decreased by only adding or removing isolators.

These and other objects, features and advantages of the present invention are specifically set forth in or will become apparent from the following detailed description of a preferred embodiment of the invention when read in conjunction with the accompanying drawing.

DESCRIPTION OF THE PREFERRED EMBODIMENT

Figure 1:
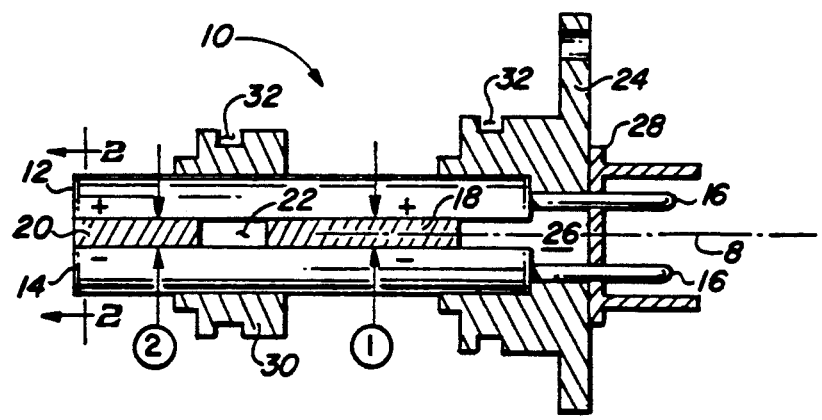
FIG. 1 is a plan view of a chip detector contemplated by the present invention.
Figure 2:
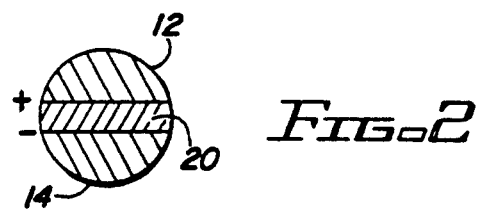
FIG. 2 is a cross-sectional view taken along line 2—2 of FIG. 1.

Referring to FIGS. 1 and 2, a dual element chip detector is generally denoted by the reference numeral 10. The chip detector 10 includes a first conductor 12 and a second conductor 14 in spaced apart, parallel relation to define a gap that extends lengthwise between the conductors 12 and 14. The longitudinal centerline of this gap is coincident with the longitudinal centerline 8 of the chip detector 10. Each of the conductors 12 and 14 has a jumper wire 16 extending from one end. The material of the conductors 12 and 14 can be any non-magnetic, conducting material.

Mounted within the gap are first and second permanent magnets 18 and 20 longitudinally spaced apart to define a space 22. The space 22 is preferably filled with a non-conducting, non-magnetic resin, but may be left empty. Each of the magnets 18, 20 are epoxy bonded to the surface portions of the conductors with which they contact. Importantly, these surface portions are machined and anodized by conventional methods to electrically isolate the magnets 18 and 20 so that electrical current cannot flow between the conductor 12 and 14 through these magnets. The poles of the magnets 18 and 20 are adjacent the conductors 12 and 14 respectfully as is depicted by the plus and minus signs. In the preferred embodiment, the thickness of the magnets is about 0.05 inches and their strength is selected to attract particles in the regions of the oil flow furthest from the magnet.

An annular housing 24 is provided having a hollow center 26 which preferably is filled with the same resin as was used to fill the space 20, but which may be left empty. Mounted to the housing's external surface is an electrical connector 28 for mating to an electric cable. The conductors 12 and 14 and magnets 18 and 20 are mounted within the housing so that the jumper wires 16 extend through the housing 24 and the electrical connector 28 so that they can be plugged into the electric cable which provides a DC voltage. The housing 24 is made of a non-conducting material, or is covered with a non-conducting coating so that it acts as an isolator. Importantly, to properly isolate the magnet 18 the housing 24 must extend sufficiently to overlap the magnet 18. A second, annular isolator 30 is mounted about the conductors 12 and 14 in the vicinity of the space 22 and extends longitudinally so as to overlap portions of both magnets 18 and 20. Both the housing 24 and the isolator 30 have a groove 32 for receiving an 0-ring for sealing between the adjacent oil flow paths. The housing 24 and isolator 30 should preferably have a minimum resistance of 100 megaohm at 100 volts DC.

Thus, the chip detector 10 has two chip elements with chip gaps 1 and 2 that can independently detect ferromagnetic particles in two separate oil flows. Currently, in the preferred embodiment, the chip detector 10 would be positioned in a gearbox or other lubrication system so that the flow of oil is parallel to the chip gaps 1 and 2 with the north pole of the magnets on the far side of the gap relative to the direction of the oil flow. However, preliminary tests conducted by the Applicant indicate that the positioning of the chip detector 10 relative with to the direction of the oil flow may not be critical to the proper functioning of the detector 10.

Figure 4:
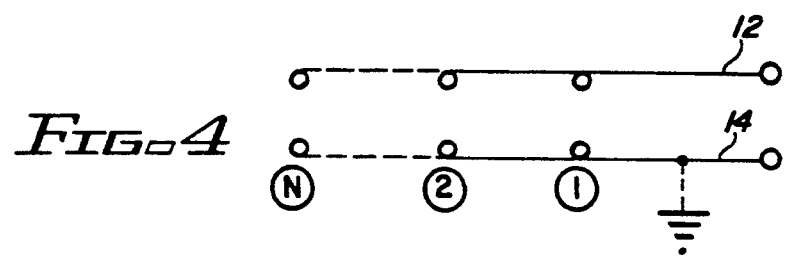
FIG. 4 is a circuit diagram of the chip detector of claims 1 and 3.

Referring to FIG. 4, as the ferromagnetic particles pass by the chip gaps 1 and 2, they are captured by the magnetic force of the magnets 18 and 20. When either a single large particle or a sufficient number of smaller particles have been captured, one or both of the chip gaps between the conductors is bridged to provide an electrical conducting path the resistance of which is low enough to permit electrical current to pass from one conductor to another which can be used to actuate a warning light on a maintenance panel. When the warning light is actuated, the chip detector 10 is removed and visually inspected to determine which oil path has excessive chips.

It is easily appreciated that with the chip detector 10 the number of chip elements can be adjusted for a particular application by simply mounting or removing magnet(s) and isolator(s) as necessary without requiring additional wiring.

Figure 3:
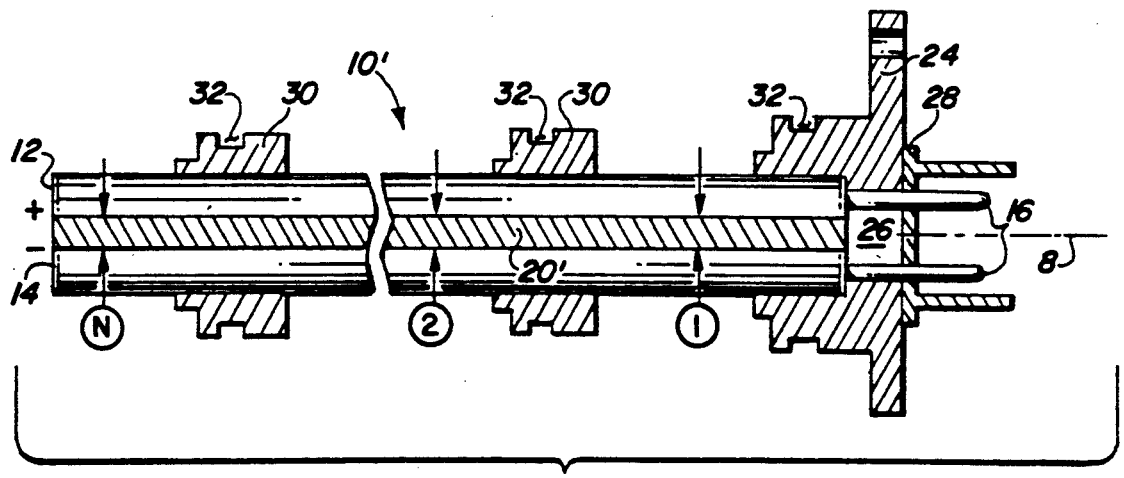
FIG. 3 is a plan view of an alternative embodiment of the chip detector contemplated by the present invention.

FIG. 3 shows a chip detector 10' which is an alternative embodiment of the present invention. Those features which are identical in both chip detectors are referenced by the same numeral.

The basic difference between the two chip detectors is that the discrete magnets 18 and 20 have been replaced by a single continuous magnet 20' that spans the longitudinal length of the conductors 12 and 14. Consequently, as shown in FIG. 4, the number of chip elements can be increased or decreased by only adding or removing isolators 30 without requiring additional circuitry with the only limitation on this number being the length of the chip detector 10'.

Various modifications and alterations to the above described chip detector will be apparent to those skilled in the art. Accordingly, the foregoing detailed description of the preferred embodiment of the invention should be considered exemplary in nature and not as limiting to the scope and spirit of the invention as set forth in the following claims.

We claim:

1. An apparatus for detecting ferromagnetic particles in one or more adjacent fluid streams in a lubrication system adapted to receive said apparatus, comprising;
    a first and second conductor in spaced apart parallel relation to define a gap that extends lengthwise therebetween, said first and second conductors mounted to a housing, which is an electrical isolator, adapted to connect said conductors with a source of electrical potential to define an open electric circuit;
    means, disposed between said conductors, for closing said electric circuit in response to a sufficient build up of said ferromagnetic particles in any of said fluid streams; and
    at least one electrically isolating member mounted about said conductors and longitudinally spaced from said housing to define at least two portions of said conductors and said closing means, said portions being electrically isolated from each other, the number of portions being equal to the number of fluid streams.

2. An apparatus for detecting ferromagnetic particles in one or more adjacent fluid streams in a lubrication system adapted to receive said apparatus, comprising;
    a first and second conductor in spaced apart parallel relation to define a gap that extends lengthwise therebetween, said first and second conductors mounted to a housing adapted to connect said conductors with a source of electrical potential to define an open electric circuit; and
    a single magnet attached to and disposed between said first and second conductors and having its positive and negative pole adjacent said first and second conductors respectfully for closing said electric circuit in response to a sufficient build up of said ferromagnetic particles in any of said fluid streams.

3. The apparatus of claim 2 wherein said magnet extends the length of said gap.

4. The apparatus of claim 3 wherein the longitudinal centerline of said gap is coincident with the longitudinal centerline of said apparatus.

5. The apparatus of claim 4 wherein the surface portions of said first and second conductors contacting said magnet are anodized to prevent electric current from flowing from one of said conductors to the other through said magnet.

6. The apparatus of claim 1 wherein said isolating member and said housing has means for preventing leakage from one of said fluid streams to another of said fluid streams.

7. The apparatus of claim 1 wherein said housing has a hollow core.

8. The apparatus of claim 7 wherein said core is filled with a non-conducting, non-magnetic resin.

9. An apparatus for detecting ferromagnetic particles in one or more adjacent fluid streams in a lubrication system adapted to receive said apparatus, comprising;
    a first and second conductor in spaced apart parallel relation to define a gap that extends lengthwise therebetween. said first and second conductors mounted to a housing adapted to connect said conductors with a source of electrical potential to define an open electric circuit; and
    a plurality of magnets longitudinally spaced apart and attached to and disposed between said first and second conductors with the positive poles and negative poles of said magnets adjacent said first and second conductors respectfully for closing said electric circuit in response to a sufficient build up of said ferromagnetic particle in any of said fluid streams.

10. The apparatus of claim 9 wherein the longitudinal centerline of said gap is coincident with the longitudinal centerline of said apparatus.

11. The apparatus of claim 10 wherein the surface portions of said first and second conductors contacting said magnets are anodized to prevent electric current from flowing from one of said conductors to the other through said magnets.

12. The apparatus of claim 9 wherein said housing is an electrical isolator.

13. The apparatus of claim 12 further comprising at least one electrically isolating member mounted about said conductors so as to circumscribe the space between said magnets.

14. The apparatus of claim 13 wherein said isolating member is of sufficient length to overlap a portion of adjacent magnets.

15. The apparatus of claim 14 wherein said isolating member and said housing has means for preventing leakage from one of said fluid streams to another of said fluid streams.

16. The apparatus of claim 12 wherein said housing has a hollow core.

17. The apparatus of claim 16 wherein said core and said spaces between said magnets are filled with a non-conducting, non-magnetic resin.

18. A method for detecting ferromagnetic particles in a plurality of adjacent fluid streams in a lubrication system, comprising the steps of;
- providing a chip detector comprising a first and second conductor in spaced apart parallel relation to define a gap that extends lengthwise therebetween, said first and second conductors mounted to a housing adapted to connect said conductors with a source of electrical potential to define an open electric circuit; and a magnet, disposed between said conductors, for closing said electric circuit in response to a sufficient build up of said ferromagnetic particle in any of said fluid streams;
- determining the number of said fluid streams;
- mounting a sufficient number of electrical isolators about and along said conductors to electrically isolate portions of said conductors and magnet from each other, the number of portions being equal to the number of said fluid streams;
- inserting said apparatus with said isolators in said lubrication system so that each of said portions is exposed to one of said fluid streams; and
- applying an electrical potential to said conductors.

* * * * *